US012241847B2

(12) United States Patent
Kot et al.

(10) Patent No.: US 12,241,847 B2
(45) Date of Patent: Mar. 4, 2025

(54) MICROWAVE SENSOR FOR IDENTIFYING THE PRESENCE OF A BIOLOGICAL MATERIAL IN A SAMPLE

(71) Applicant: LIVERPOOL JOHN MOORES UNIVERSITY, Liverpool (GB)

(72) Inventors: Patryk Kot, Liverpool (GB); Magomed Muradov, Liverpool (GB); Andrew Shaw, Liverpool (GB); Kah Hou Teng, Liverpool (GB)

(73) Assignee: LIVERPOOL JOHN MOORES UNIVERSITY, Merseyside (GB)

( * ) Notice: Subject to any disclaimer, the term of this patent is extended or adjusted under 35 U.S.C. 154(b) by 172 days.

(21) Appl. No.: 17/756,025

(22) PCT Filed: Oct. 23, 2020

(86) PCT No.: PCT/GB2020/052691
§ 371 (c)(1),
(2) Date: May 13, 2022

(87) PCT Pub. No.: WO2021/094707
PCT Pub. Date: May 20, 2021

(65) Prior Publication Data
US 2022/0404293 A1 Dec. 22, 2022

(30) Foreign Application Priority Data

Nov. 15, 2019 (GB) ..................................... 1916716

(51) Int. Cl.
*G01N 22/00* (2006.01)
*G01N 33/483* (2006.01)
(52) U.S. Cl.
CPC ........... *G01N 22/00* (2013.01); *G01N 33/483* (2013.01)

(58) Field of Classification Search
CPC ............................ G01N 22/00; G01N 33/483
(Continued)

(56) References Cited

U.S. PATENT DOCUMENTS

| 2018/0292525 A1* | 10/2018 | Smith | ................ | G01S 7/411 |
| 2019/0227003 A1* | 7/2019 | Ghasr | ................ | G07D 7/1205 |

(Continued)

FOREIGN PATENT DOCUMENTS

| GB | 2428801 A | 2/2007 |
| JP | 2007271412 A | 10/2007 |

(Continued)

OTHER PUBLICATIONS

Teng et al. "Non-destructive Electromagnetic Wave Sensor for Hazardous Biological Materials" (Additional Copy), 2019 (Year: 2019).*

(Continued)

*Primary Examiner* — Raul J Rios Russo
(74) *Attorney, Agent, or Firm* — Hoffman Warnick LLC

(57) ABSTRACT

Disclosed is a sensor for identifying the presence of a biological material in a sample, the sensor comprising: an antenna apparatus for transmitting and receiving microwave electromagnetic (EM) signals; a signal transmitter apparatus coupled to the antenna apparatus and arranged to transmit a microwave-frequency output signal to the antenna apparatus for emission therefrom as an output electromagnetic (EM) signal for reflection at a said sample and to receive a microwave-frequency return signal from the antenna apparatus in response to a return electromagnetic (EM) signal received thereat by reflection from a said sample; a signal processor arranged to calculate a complex-valued reflection coefficient, comprising a real component and an imaginary component, according to said return signal and said output signal, and to detect the presence of said biological material (Continued)

in said sample according to both the real component and the imaginary component of said reflection coefficient.

20 Claims, 8 Drawing Sheets

(58) Field of Classification Search
USPC .......................................................... 324/638
See application file for complete search history.

(56) References Cited

U.S. PATENT DOCUMENTS

| 2020/0348410 | A1* | 11/2020 | Smith | G01S 7/411 |
| 2021/0030305 | A1* | 2/2021 | Nikolayev | A61B 5/0507 |
| 2022/0192546 | A1* | 6/2022 | Palikaras | A61B 5/053 |
| 2024/0081671 | A1* | 3/2024 | El Hajj | A61B 5/05 |

FOREIGN PATENT DOCUMENTS

| WO | 2011100390 A1 | 8/2011 |
| WO | 2018168499 A1 | 9/2018 |

OTHER PUBLICATIONS

PCT International Search Report and Written Opinion for International Application No. PCT/GB2020/052691, dated Feb. 16, 2021, 11 pages.
Great Britain Search Report for Application No. GB1916716.2, dated Mar. 30, 2020, 2 pages.
Teng et al., "Non-destructive Electromagnetic Wave Sensor for Hazardous Biological Materials," 2019 12th International Conference on Developments in Esystems Engineering, Oct. 7, 2019, pp. 651-655.

* cited by examiner

MICROWAVE SENSOR FOR IDENTIFYING THE PRESENCE OF A BIOLOGICAL MATERIAL IN A SAMPLE

FIELD

The invention relates to sensors for identifying the presence of a biological material in a sample.

BACKGROUND

There are numerous techniques for chemical and biological monitoring. Examples included fluorescence microscopy, mass spectrometry, gas chromatography and matrix-assisted laser desorption ionization (MALDI). These techniques involve the use of analytical instruments which must be operated by highly skilled and trained technicians in order to obtain useful results. Moreover, the instruments are costly to manufacture and require regular maintenance in the laboratory.

Biosensors for the detection of biological materials have been discussed in the field. However, commercially available devices are complex to operate and similarly require highly skilled and trained technicians in order to operate them. Known devices are large, require a mains power supply, regular maintenance and a constant supply of reagents. They are also slow at analysing samples.

It is an object of embodiments of the present invention to provide an alternative biosensor for the detection of biological materials and/or to address one or more of the problems highlighted above.

SUMMARY

According to the present invention there is provided an apparatus and method as set forth in the appended claims. Other features of the invention will be apparent from the dependent claims, and the description which follows.

In a first aspect, the invention provides a sensor for identifying the presence of a biological material in a sample, the sensor comprising:
  an antenna apparatus for transmitting and receiving microwave electromagnetic (EM) signals;
  a signal transmitter apparatus coupled to the antenna apparatus and arranged to transmit a microwave-frequency output signal to the antenna apparatus for emission therefrom as an output electromagnetic (EM) signal for reflection at a said sample and to receive a microwave-frequency return signal from the antenna apparatus in response to a return electromagnetic (EM) signal received thereat by reflection from a said sample;
  a signal processor arranged to calculate a complex-valued reflection coefficient, comprising a real component and an imaginary component, according to said return signal and said output signal, and to detect the presence of said biological material in said sample according to both the real component and the imaginary component of said reflection coefficient.

Existing methods for detecting the presence of specified materials in a sample, using microwave EM signals, typically use the value of a transmission coefficient (e.g. the S-parameter: $S_{21}$). Furthermore, established convention and prejudice in the field dictates that only the real component of a complex-valued S-parameter transmission coefficient (e.g. $S_{21}$) can convey diagnostic information, with the imaginary component being discarded. As will be readily understood by the person of ordinary skill in the art, an 'S-parameter' is generally a complex-valued quantity: $S_{xy}=S_{Real}+jS_{imaginary}$ (where j is the square root of $-1$, and X,Y are 1 or 2).

Surprisingly, the inventors have discovered that the use of the reflection coefficient (e.g. the S-parameter: $S_{11}$) and in particular the use of both the real component and the imaginary component of the complex-valued reflection coefficient, reveals a wealth of useful diagnostic information regarding biological sample concentration within a sample.

Desirably, the signal processor apparatus is arranged to subtract a value of a first background component from the value of said real component thereby to generate an adjusted real component of said reflection coefficient, and to subtract a value of a second background component from the value of said imaginary component thereby to generate an adjusted imaginary component of said reflection coefficient, and to detect the presence of said biological material in said sample according to both the adjusted real component and the adjusted imaginary component of said reflection coefficient.

Desirably, the first background component and the second background component are the real component and the imaginary component, respectively, of a complex-valued background reflection coefficient stored in the signal processor and corresponding to the absence of said biological material in a sample.

Desirably, the adjusted real component and the adjusted imaginary component of said reflection coefficient define a complex vector which is the vector sum of the complex-valued reflection coefficient and the complex-valued background reflection coefficient. This adjustment, in any aspect of the invention, is preferably done with in respect of a signal frequency (v) common to both the reflection coefficient and the background reflection coefficient. The invention, in any aspect, may include calculation by application of the following equation:

$$|S_{11}|_{v=i} = \sqrt{\begin{array}{l}(\text{Re}(Sample_i) - \text{Re}(Background_i))^2 + \\ (\text{Im}(Sample_i) - \text{Im}(Background_i))^2\end{array}}$$

Here, the index (i) refers to a particular selected microwave signal frequency (v), or a narrow band of frequencies centred on a desired frequency (v=i), and the terms "Sample" and "Background" refer to the values of the input signals received by the signal transmitter apparatus, respectively. Also, the symbols "Re" and "Im" refer to the real component and the imaginary component, respectively.

Desirably, the microwave-frequency output signal and the microwave-frequency return signal share the same signal frequency.

Preferably, the signal frequency is in the range from 1.0 GHz to 6.0 GHz.

The signal transmitter apparatus may comprise a signal transceiver unit configured to both transmit said output signal to said antenna apparatus and to receive said return signal from said antenna apparatus.

The antenna apparatus may comprise a single antenna arranged to emit said output electromagnetic (EM) signal and to receive said return electromagnetic (EM) signal.

Desirably, the antenna apparatus comprises a manually operable hand-held antenna assembly. The EM microwave radiation is preferably emitted and collected with the same antenna. The antenna apparatus preferably comprises a directional antenna.

Desirably, the biological material comprises dipicolinc acid (DPA).

Desirably, the signal processor comprises an RF signal generator (e.g. Vector Network Analyser or Integrated Circuit). An RF signal generator provides a known stimulus signal to a sample under scrutiny and multiple receivers to measure the response. The RF signal generator preferably forms a closed loop, allowing it to measure the electrical magnitude and phase response of components accurately.

S-parameter: $S_{xy}=S_{Real}+jS_{imaginary}$ (where j is the square root of $-1$). The reflection and transmission measurements are defined in terms of scattering parameters, or S-parameters. For a 2-port network, four fundamental S-parameters can be measured, and they are defined as $S_{XY}$. For a 2-port VNA, measurements of signals leaving Port 1 are called forward measurements, and those leaving Port 2 are called reverse measurements. Signals that leave and return to the same port are designated reflection measurements, and those that leave one port and return to another port are designated transmission measurements. S-parameters are an abbreviated designation for these measurements, and are used as shown in the following list:

$S_{11}$: Forward Reflection represents the measurement in which the signal leaves port 1 and is reflected back to port 1.

$S_{21}$: Forward Transmission represents the measurement in which the signal leaves port 1 and is transmitted to port 2.

$S_{12}$: Reverse Transmission represents the measurement in which the signal leaves port 2 and is transmitted to port 1.

$S_{22}$: Reverse Reflection represents the measurement in which the signal leaves port 2 and is reflected back to port 2.

The first number (X) in $S_{XY}$ is the port number into which the signal is being injected, and the second number (Y) is the port number from which the signal is leaving. The S-parameter is a ratio of these two signals.

The incident waves are designated as an and the reflected waves are designated as bn where n is the port number. Both 'a' and 'b' waves are phasors, having both magnitude and phase at the specified terminals of the network port. First, a portion of the stimulus signal is taken as a reference signal. S-parameters are defined as ratios of signals coming from various ports relative to this reference. At the same time, some of the stimulus signal ($a_1$) is reflected as it enters the sample ($b_1$). The portion of the input signal that is reflected is measured with a receiver connected to Port 1 inside the VNA. The following table summarises these definitions:

| | Forward: | Reverse: |
|---|---|---|
| Reflection: | $S_{11} = \dfrac{\text{Reflected}}{\text{Incident}} = \dfrac{b_1}{a_1}\bigg|_{a_2=0}$ | $S_{22} = \dfrac{\text{Reflected}}{\text{Incident}} = \dfrac{b_2}{a_2}\bigg|_{a_1=0}$ |
| Transmission: | $S_{21} = \dfrac{\text{Transmitted}}{\text{Incident}} = \dfrac{b_2}{a_1}\bigg|_{a_2=0}$ | $S_{12} = \dfrac{\text{Transmitted}}{\text{Incident}} = \dfrac{b_1}{a_2}\bigg|_{a_1=0}$ |

The identifying of the presence of a biological material in a sample may comprise identifying the concentration of the biological material (e.g. molar concentration).

In a second aspect, the invention provides a method for identifying the presence of a biological material in a sample, the method comprising:

by and an antenna apparatus, transmitting and receiving microwave electromagnetic (EM) signals;

by a signal transmitter apparatus coupled to the antenna apparatus:

transmitting a microwave-frequency output signal to the antenna apparatus for emission therefrom as an output electromagnetic (EM) signal for reflection at a said sample;

receiving a microwave-frequency return signal from the antenna apparatus in response to a return electromagnetic (EM) signal received thereat by reflection from a said sample;

by a signal processor, calculating a complex-valued reflection coefficient, comprising a real component and an imaginary component, according to said return signal and said output signal, and detecting the presence of said biological material in said sample according to both the real component and the imaginary component of said reflection coefficient.

The method may include, by the signal processor: subtracting a value of a first background component from the value of said real component thereby to generate an adjusted real component of said reflection coefficient; and, subtracting a value of a second background component from the value of said imaginary component thereby to generate an adjusted imaginary component of said reflection coefficient; and. detecting the presence of said biological material in said sample according to both the adjusted real component and the adjusted imaginary component of said reflection coefficient.

Desirably, in the method, the first background component and the second background component are the real component and the imaginary component, respectively, of a complex-valued background reflection coefficient corresponding to the absence of said biological material in a sample.

Preferably, the adjusted real component and the adjusted imaginary component of said reflection coefficient define a complex vector which is the vector sum of the complex-valued reflection coefficient and the complex-valued background reflection coefficient.

Desirably, the microwave-frequency output signal and the microwave-frequency return signal share the same signal frequency. Preferably, the signal frequency is in the range from 1.0 GHz to 6.0 GHz.

The method may include emitting said output electromagnetic (EM) signal and receiving said return electromagnetic (EM) signal via a common single antenna. The method may include emitting said output electromagnetic (EM) signal and receiving said return electromagnetic (EM) signal via a manually operable hand-held antenna assembly. The method may include emitting said output electromagnetic (EM) signal and receiving said return electromagnetic (EM) signal via directionally via a directional antenna.

Preferably, in the method, the biological material comprises dipicolinc acid (DPA).

In a third aspect, the invention may provide a method for identifying the presence of a biological material in a sample, the method comprising the steps of: generating EM radiation using a transmitted electrical signal at a transmitter; generating a reflected electrical signal at a receiver in response to the received EM signal at the receiver; generating a comparative electrical signal by comparing the transmitted electrical signal with the reflected electrical signal; extracting real and imaginary components of the comparative electrical signal; calculating the concentration of the biological material according to both the real components and imaginary components of the comparative signal.

In a fourth aspect, the invention may provide a method for identifying the presence of a biological material in a sample, the method comprising the steps of: performing a detection process on a sample of interest to collect a first spectrum; comparing the first spectrum with a background spectrum;

identifying one or more regions of interest; and comparing data from the regions of interest with calibration data, the detection process comprising the steps of: providing an output signal of known frequency; generating EM radiation using that signal; irradiating the sample with the EM radiation; receiving reflected radiation from the sample; generating a reflected signal using the reflected radiation; and comparing the output signal with the reflected signal.

BRIEF DESCRIPTION OF DRAWINGS

For a better understanding of the invention, and to show how embodiments of the same may be carried into effect, reference will now be made, by way of example only, to the accompanying diagrammatic drawings in which.

DESCRIPTION OF EMBODIMENTS

Figure 1:
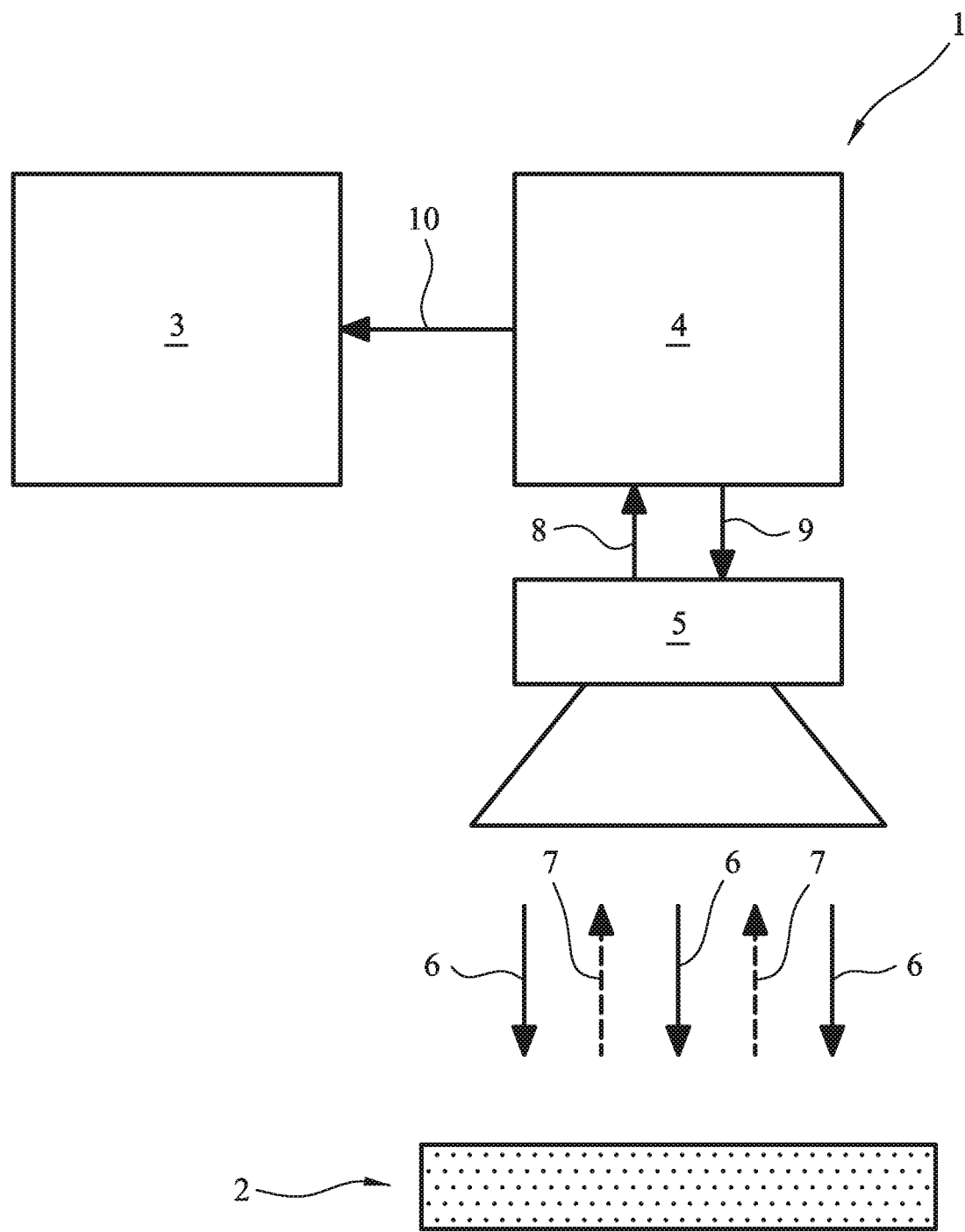
FIG. 1 schematically illustrates a sensor according to an embodiment of the invention.
Figure 2:
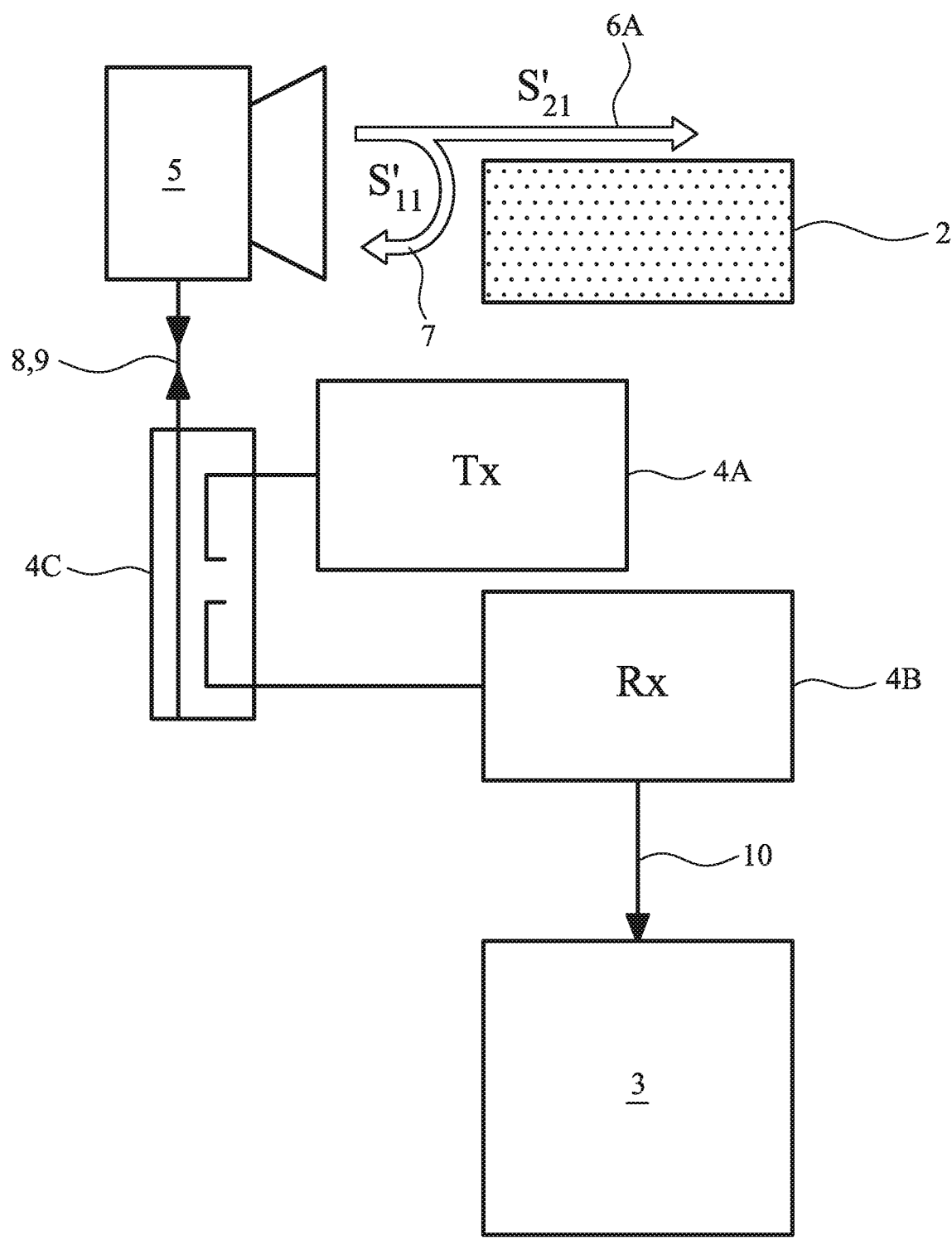
FIG. 2 schematically illustrates the sensor of FIG. 1 in more detail.

Referring to FIG. 1 there is illustrated a sensor (1) for identifying the presence of a biological material in a sample. The centre includes a single directional antenna, in the form of a hand-held horn antenna (5) adapted for transmitting (6) and receiving (7) microwave electromagnetic (EM) signals. The centre also includes a transceiver apparatus (4), which may take the form of an RF signal generator (e.g. a Vector Network Analyser (VNA) or Integrated Circuit), which is coupled to the directional antenna (5) via suitable microwave-frequency signal transmission lines (8, 9) and is arranged to transmit a microwave-frequency output signal (9) to the directional antenna for emission as a microwave (EM) signal (6) directed towards a sample (2) within which it is desired to identify the presence/absence of a specified biological material.

The directional antenna is arranged for receiving a reflected component (7) of the output electromagnetic microwave signal. The transceiver apparatus (4) is arranged to receive a microwave-frequency return signal from the directional antenna in response to the returned electromagnetic signal received at the antenna, and to output an electrical/electronic receiver signal (10) in response to the received return signal.

The microwave frequency output signal and the microwave frequency return signal share the same signal frequency, which is a frequency in the range 1.0 GHz to 6.0 GHz, such as 2.4 GHz, or such as 4.58 GHz.

The sensor also includes a signal processing unit (3) arranged to receive the electrical/electronic receiver signal (10) and to calculate a complex-valued reflection coefficient in the form of a scattering matrix element ($S'_{11}$) according to the following equation:

$$S'_{11} = \text{Re}(S'_{11}) + jIm(S'_{11})$$

It is noted that the reflection coefficient comprises a real component and an imaginary component. The signal processing unit also stores within a data memory store, a complex-valued background scattering matrix element ($\hat{S}_{11}$):

$$\hat{S}_{11} = \text{Re}(\hat{S}_{11}) + jIm(\hat{S}_{11})$$

The signal processor is arranged to subtract the real component of the background scattering matrix element ($\hat{S}_{11}$) from the real component of the calculated scattering matrix element ($S'_{11}$), and to subtract the imaginary component of the background scattering matrix element ($\hat{S}_{11}$) from the imaginary component of the calculated scattering matrix element ($S'_{11}$). The effect is to generate the real component and imaginary component of an adjusted scattering matrix element, $\overline{S_{11}}$, where:

$$\overline{S_{11}} = \text{Re}(S'_{11} - \hat{S}_{11}) + jIm(S'_{11} - \hat{S}_{11})$$

The background scattering matrix element corresponds to a previously-calculated scattering matrix element that has been determined in respect of previously reflected EM microwave radiation (at the same frequency as the present EM radiation) in respect of the same simple material in the known absence of any of the biological material presently being sensed. The signal processor is further arranged to calculate the following real-valued scattering matrix element magnitude value ($|S_{11}|$) using the real and imaginary component values of the complex-valued adjusted scattering matrix element, as follows:

$$|S_{11}| = \sqrt{[\text{Re}(S'_{11}) - \text{Re}(\hat{S}_{11})]^2 + [\text{Im}(S'_{11}) - \text{Im}(\hat{S}_{11})]^2}$$

The signal processor is arranged to detect the presence of the specified biological material within the sample, according to the value of the above real-valued scattering matrix element value ($|S_{11}|$). In this way, the signal processor, and the sensor as a whole, is arranged to identify the presence of the biological material within the sample according to both the real component and the imaginary component of the reflection coefficient obtained from the sample.

Figure 7:
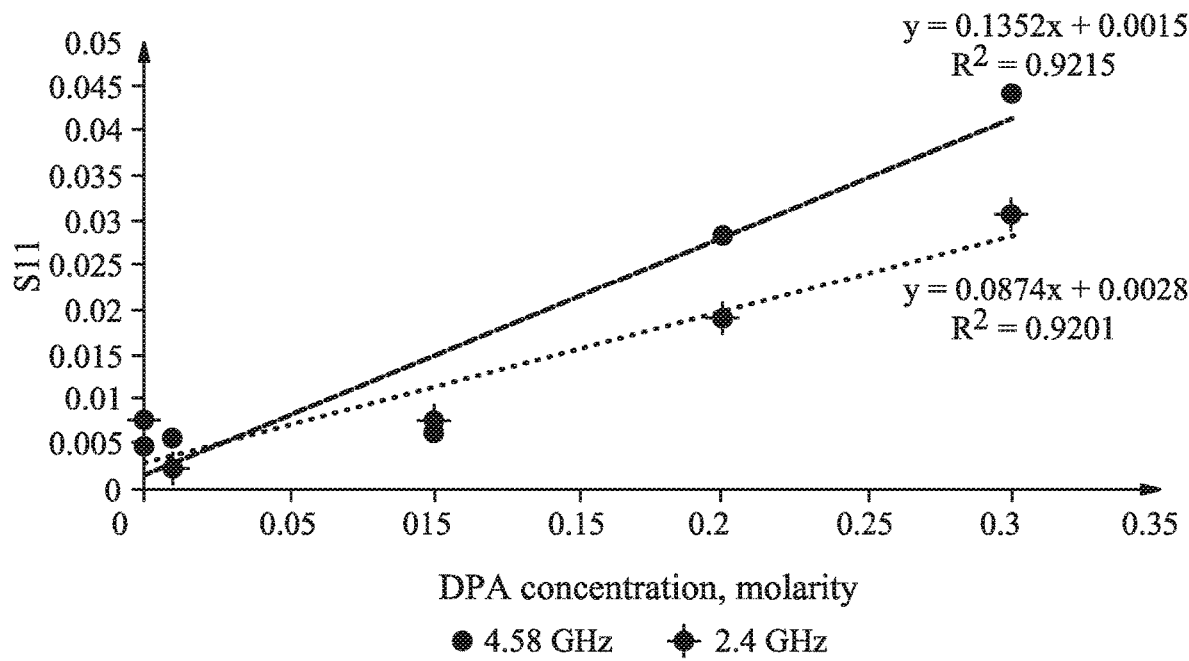
FIG. 7 illustrates a correlation trend line of a reflection coefficient ($S_{11}$) vs DPA concentration within a sample containing multiple different molar concentrations of DPA within NaOH solvent (1M NaOH)
Figure 8:
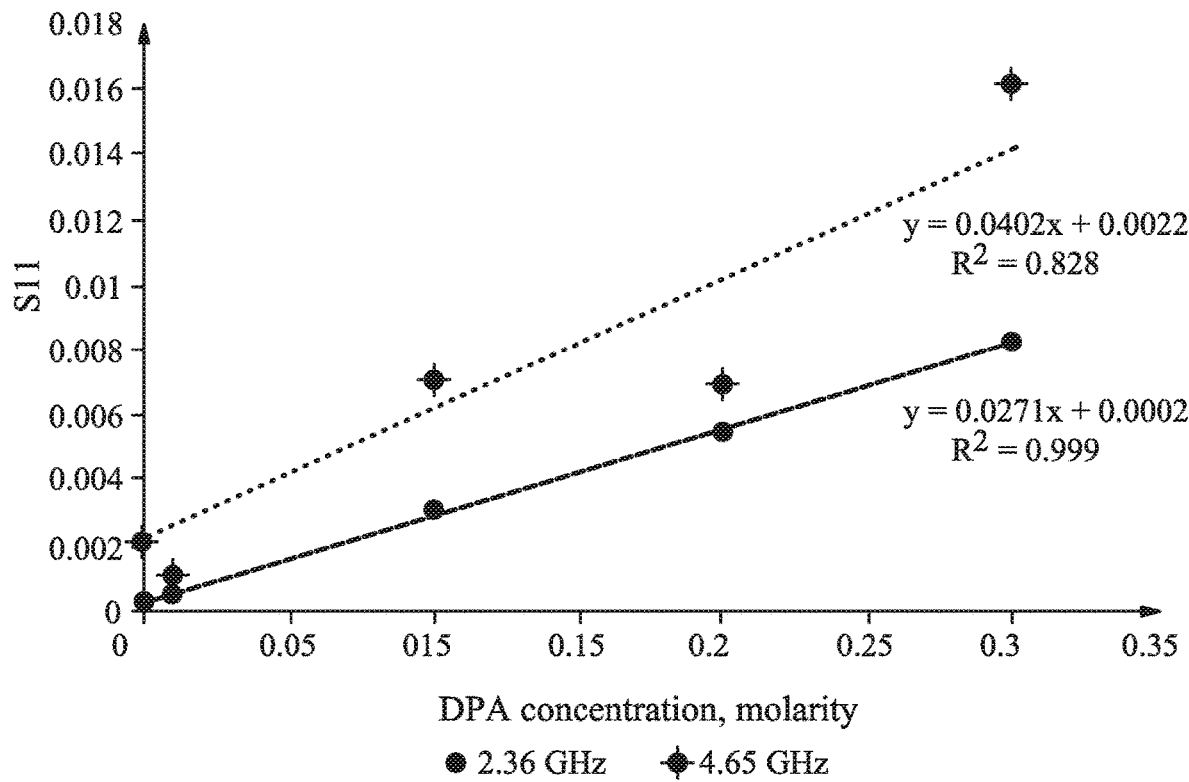
FIG. 8 illustrates a correlation trend line of a reflection coefficient ($S_{11}$) vs DPA concentration within a sample containing multiple different molar concentrations of DPA within DMSO solvent.

In particular, it has been found that the value of real-valued scattering matrix element value ($|S_{11}|$), correlates in a statistically significant way with the molar concentration of the specified biological material within the sample. FIG. 7 and FIG. 8 graphically illustrate this correlation in respect of the molar concentration of the biological material (i.e. DPA), in respect of four different microwave EM signal frequencies, namely: 2.26 GHz; 2.4 GHz; 4.58 GHz; 4.65 GHz. At each of these four frequencies, a substantially linear and statistically significant correlation exists between the value of the real-valued scattering matrix element value ($|S_{11}|$), and the molar concentration of the biological material within the sample.

The signal processor is arranged to output a detection result in accordance with a predetermined linear regression form:

$$\text{Concentration} = m_v \cdot |S_{11}| + c_v$$

Here, $m_v$ is a pre-calibrated linear regression gradient value associated with a given microwave signal frequency (v), and $c_v$ is a pre-calibrated linear regression intercept value associated with the given microwave signal frequency. The signal processor may be arranged to issue an alarm signal if a value of concentration is detected which exceeds a pre-set threshold value.

It is schematically illustrates the sensor (1) in more detail in which components of the signal transceiver unit (4) are shown. In particular, a transmitter unit (4A) of the transceiver and a separate receiver unit (4B) of the transceiver are each coupled to a signal transmission line by a coupler unit (4C) the rate transmitted and received microwave-frequency output/return signals to be communicated between the transceiver unit and the hand-held directional antenna (5). An output electromagnetic (EM) directed upon the sample (2) is partially reflected from the sample (2) as a return EM signal (7) according to a reflection coefficient $S'_{11}$, and is partially transmitted through the sample according to a forward transmission coefficient $S'_{21}$.

A novel non-destructive electromagnetic wave (EM) sensor for rapid identification of biological material is disclosed. Biological threats include biological agents such as bacteria spores, viruses and toxins etc. Spores can disable or kill people, animals and crops. Therefore, it is important to identify the hazard in rapid and non-destructive manner to make a safer environment. In this disclosure, in a preferred embodiment, a 2.45 GHz microwave source is used to exemplify the invention as applied to the detection of dipliconic acid (DPA), which is the bio-maker of bacillus spores. Of course, it is to be understood that this embodiment is selected for permitting a better understanding of the invention, which is not limited to detection of DPA alone.

Results are presented for detecting DPA from 0.001 M-0.3 M concentration at a microwave signal frequency of 2.4 GHz. In addition, different species of bacillus spores are detectable at microwave frequencies of approximately 2.36 GHz. The results demonstrate that a electromagnetic wave sensor, according to the invention, may be use as a non-destructive and real-time sensor to detect bacillus spores.

Significant outbreaks of disease are among the highest impact risks faced by any society, threatening lives and causing disruption to public services and the economy. Government agencies recognize the importance of intervening early to prevent biological threats from emerging, or from spreading once they emerge. Large-scale disease outbreaks in animals or plants can be equally significant in terms of economic, environmental and social impact.

There is a wide range of instrumentation available for chemical/biological monitoring. However, the existing technologies mostly are analytical instruments which require highly skilled and trained workers and are costly to manufacture and maintain in a laboratory. Examples include fluorescence spectroscopy, mass spectrometry, gas chromatography and matrix-assisted laser desorption ionization (MALDI). However, commercially available devices are large and require mains power, regular maintenance and constant supply of reagents to operate. In addition, provided systems are complex to operate and require time for sample analysis.

The present disclosure focuses on *Bacillus* species (*Bacillus globigii*, *Bacillus thuringiensis*), purely as an illustrative but non-limiting, example. Bacillius globigii and *Bacillus thuringiensis* are spore-forming bacterial species. Both are used as surrogates for analysis of the potential properties of *Bacillus anthracis* spores. *Bacillus thuringiensis* is also used as an insecticide on a large scale. Pyridine-2,6-dicarboxylic acid (dipicolinic acid, DPA) is a unique constituent of all endospores from *Bacillus* and *Clostridium* species, and represents a substantial amount of the dry weight in bacterial spores (e.g. 5%-14%) DPA is localized in the spore core, and chelated with divalent cations. It has never been detected in vegetative cells. DPA is thus often used to detect the presence of bacterial spores. Hence they are often referred to as biomarkers.

The present disclosure, in exemplary embodiments, refers to detection dipicolinc acid (DPA) using a 2.45 GHz microwave antenna. This work was conducted to demonstrate the concept of employing electromagnetic wave capable of detecting different concentrations of DPA contained in a wet sample. The example given is in relation to a wet sample, but it is to be understood that the invention may be applied equally to detecting different concentrations of DPA and other chemicals, or other biological materials, in a dry sample or a wet sample, equally. A good understanding of the characterization and unique signal spectrum of the DPA and varied concentration is possible using the wet and/or dry-based sampling analysis. The invention, in preferred embodiments, may provide a non-destructive electromagnetic sensor for instant identification of hazardous biological material.

EXPERIMENTAL PREPARATION AND METHODOLOGY

Microwave Theory and Application

Materials can be studied from the measurement of their interactions with microwaves. This interaction can be realised in the form of a unique signal spectrum known as reflection coefficient ($S_{11}$). Generally, these measurement quantities vary with the change in parameters such as permittivity and conductivity of the materials. Permittivity is a measurement of the response of a dielectric medium to the applied microwaves that can be detected through its changing electric field. It depends on the material's ability to polarise in response to the applied field. The two primary parameters that define permittivity are known as dielectric constant and dielectric loss of material.

(i) Dielectric constant ($\varepsilon'$): The phenomena of energy storage and reduction in the wave velocity when EM waves pass through the material which is used to distinguish dielectric constant values of different materials. Different dielectric constant values are observed, because of the changes in polarisation inside the material.

(ii) Dielectric loss ($\varepsilon''$): The loss of electromagnetic energy propagating inside a dielectric material. The reduction of the wave magnitude is due to the rotation and oscillation of the molecules in response to the applied electric field and loss of energy owing to intermolecular interactions.

Changes in the materials' concentration, type, percentage etc. will be followed by changes in its permittivity, yielding a unique signal spectrum when it interacts with microwave radiation. In this way, the material is characterised over the range of discrete frequencies.

Data Acquisition and Analysis

Experiments were conducted to measure samples with different DPA concentrations. All microwave measurements were carried out by emitting from an antenna a microwave EM probe wave into a sample under investigation, and measuring only the reflected signal ($S_{11}$) using the antenna. Here, the RF signal generator was an R&S®ZNB 20 Vector Network Analyser (VNA), 100 kHz-20 GHz (Rohde & Schwarz). The invention is not limited to the use of a VNA, and other RF signal generators may be used. In this example, a VNA was used to transmit the microwave signal to the antenna for radiating an microwave EM probe wave and to capture the reflected microwave EM wave received at the antenna in response. The measurements were recorded in the on board memory of the VNA.

A microwave input power of 1 mW (0 dBm) was launched into the sensor antenna. The sensor antenna was a hand held unit that enabled measurements over a wide area.

To analyse the acquired reflection coefficient ($S_{11}$) of given sample under investigation, both the dielectric constant and dielectric loss of the material were characterized. In addition, the reflection coefficient ($S_{11}$) acquired from the base solvent (NaOH and DMSO) with no DPA present, was subtracted from the reflection coefficient ($S_{11}$) acquired from the base solvent (NaOH and DMSO) with a non-zero concentration of DPA present. This subtraction was applied to both the magnitude and phase of the complex number representing the respective acquired reflection coefficient ($S_{11}$). Regression analysis of the acquired reflection coefficient magnitude value ($|S_{11}|$) of a sample, at a given fixed probe signal EM frequency, as a function of changing DPA concentration, was performed.

RESULTS AND DISCUSSION

Figure 3:
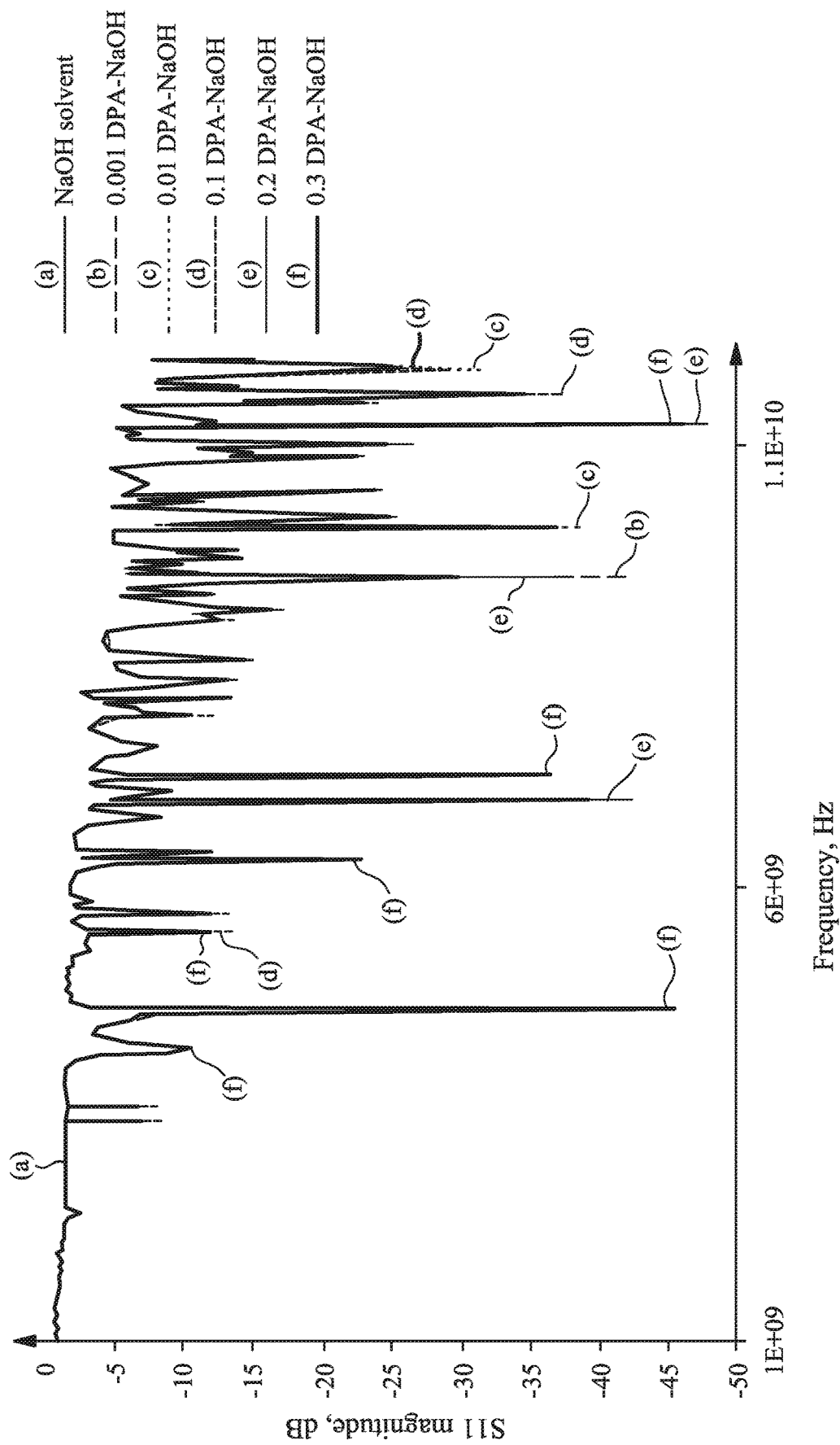
FIG. 3 illustrates multiple spectra of the magnitude of a reflection coefficient ($S_{11}$) of microwave radiation reflected from a sample containing, respectively, multiple different concentrations of DPA within NaOH solvent.

Acquired reflection coefficient measurements ($S_{11}$), comprising both real component of $S_{11}$ and imaginary component of $S_{11}$, for samples comprising DPA-within-NaOH and for samples comprising DPA-within-DMSO, were obtained from the VNA. FIG. 3 shows the frequency spectrum of the scalar magnitude of $S_{11}$ (i.e. the value of $|S_{11}|$, as a function of changing microwave probe signal frequency) over the spectral range of 1 GHz to 12 GHz, for samples comprising DPA-within-NaOH ("DPA-NaOH").

Figure 4:
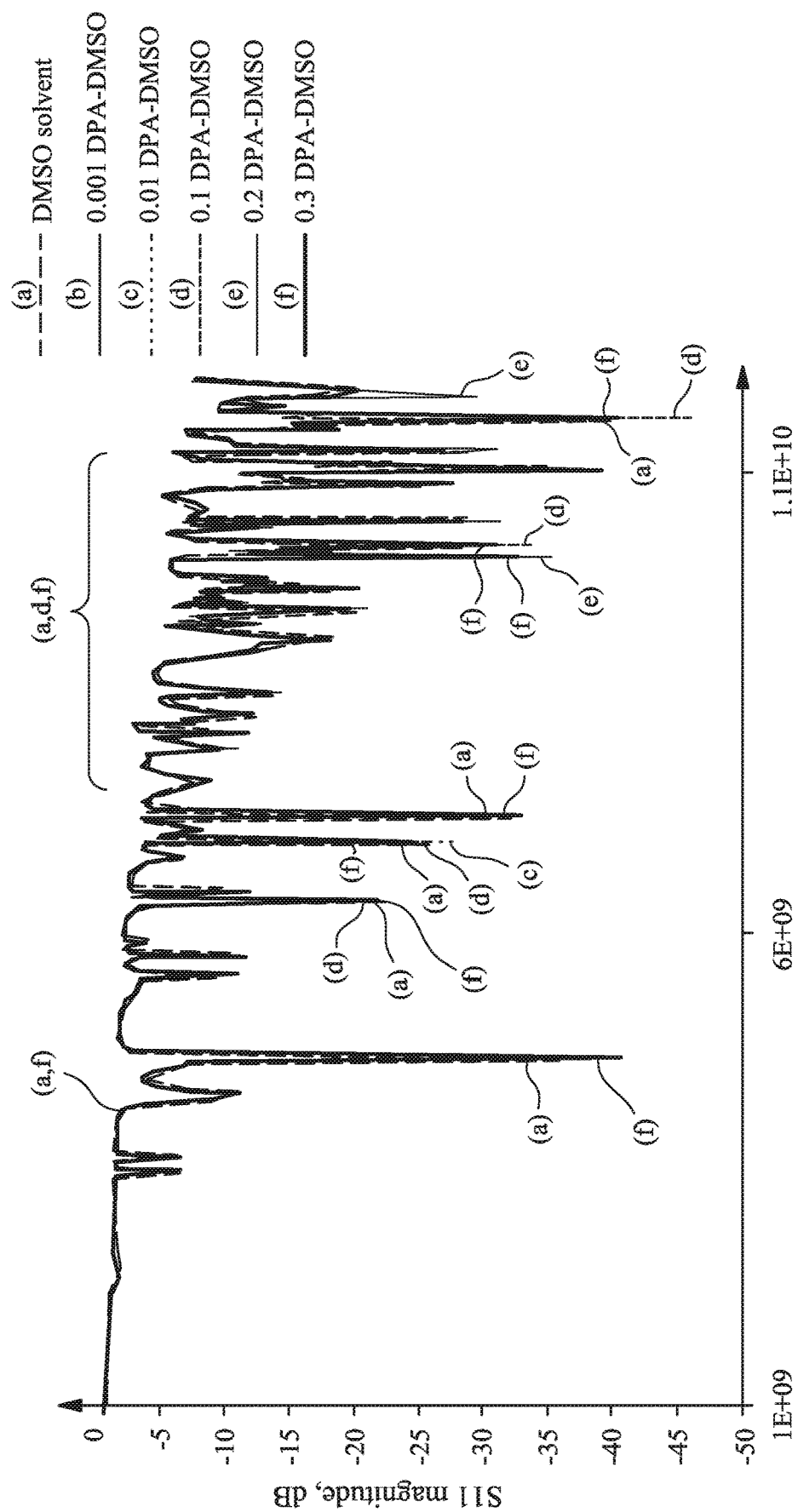
FIG. 4 illustrates multiple spectra of the magnitude of a reflection coefficient ($S_{11}$) of microwave radiation reflected from a sample containing, respectively, multiple different concentrations of DPA within DMSO solvent.

FIG. 4 shows the frequency spectrum of the scalar magnitude of $S_{11}$ (i.e. the value of $|S_{11}|$, as a function of changing microwave probe signal frequency) over the spectral range of 1 GHz to 12 GHz, for samples comprising DPA-within-DMSO ("DPA-DMSO").

Figure 5:
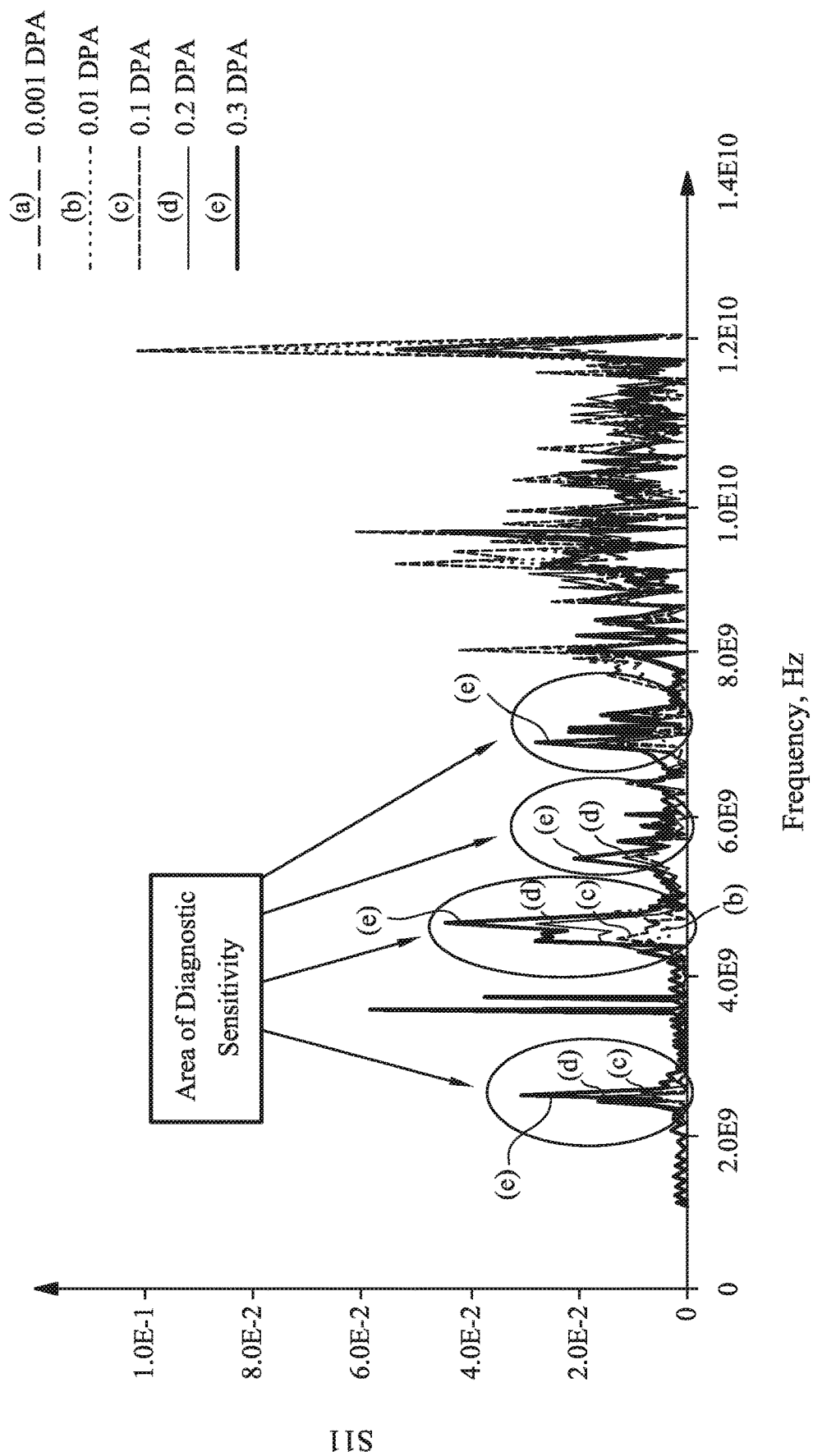
FIG. 5 illustrates multiple spectra of the magnitude of an adjusted reflection coefficient (S11) of microwave radiation reflected from a sample containing, respectively, multiple different concentrations of DPA within NaOH solvent.
Figure 6:
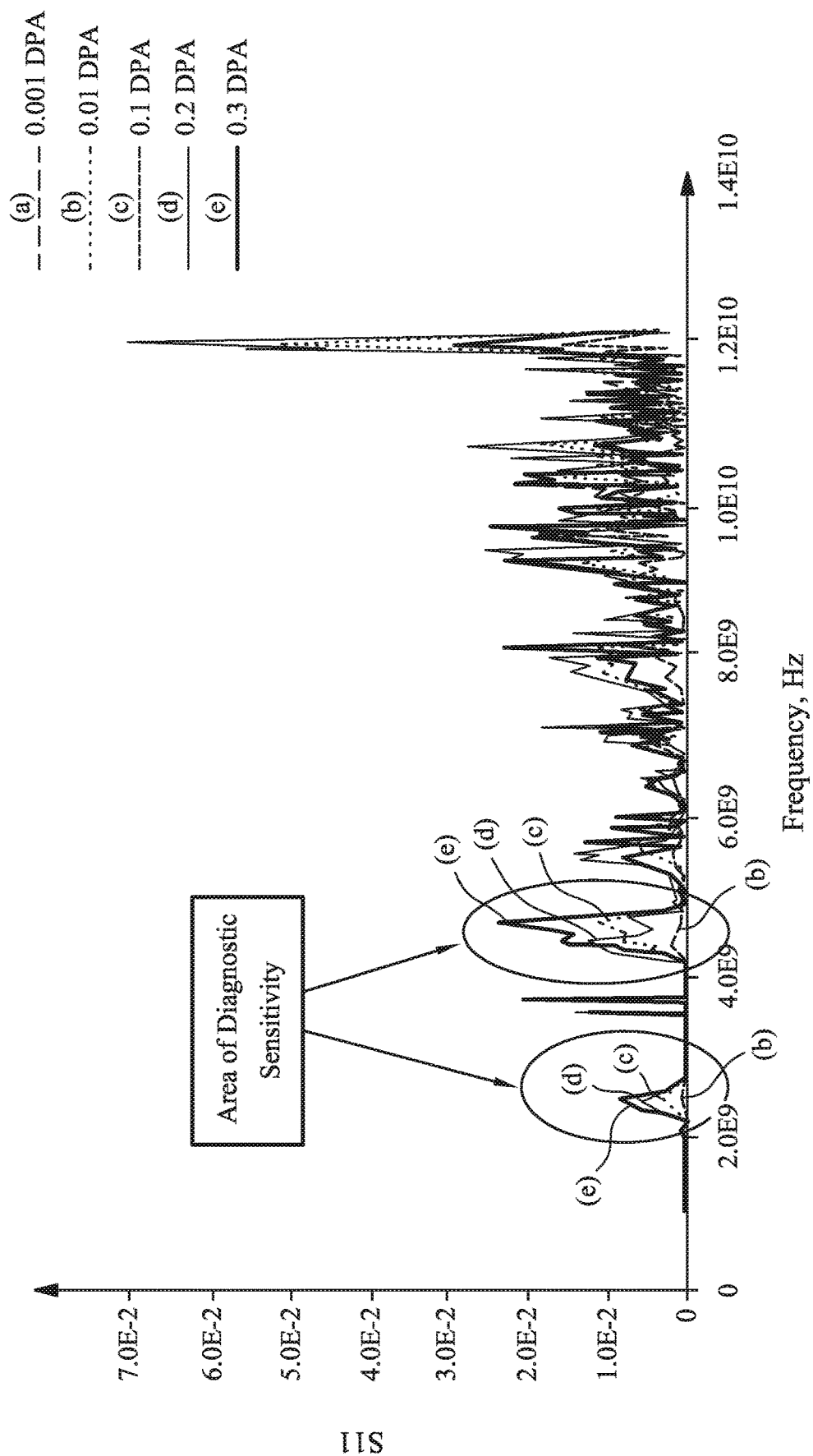
FIG. 6 illustrates multiple spectra of the magnitude of an adjusted reflection coefficient (S11) of microwave radiation reflected from a sample containing, respectively, multiple different concentrations of DPA within DMSO solvent.

FIG. 5 and FIG. 6 each show the adjusted measurements generated by deducting signal spectra using the following equation:

$$|S_{11}|_{v=i} = \sqrt{\frac{(\text{Re}(Sample_i) - \text{Re}(Background_i))^2 + }{(\text{Im}(Sample_i) - \text{Im}(Background_i))^2}}$$

FIG. 5 and FIG. 6, show multiple spectra for varied concentrations of DPA were subtraction from a background spectrum of pure NaOH or DMSO solvent has been performed to generate adjusted measurements. This reveals microwave frequencies that show diagnostic sensitivity to detection of the biological material, from 1-12 GHz in 20,000 data points. In particular, FIG. 5 shows $S_{11}$ measurements of DPA subtract from $S_{11}$ measurements of a based-fluid of 1 Mole NaOH, whereas FIG. 6 shows $S_{11}$ measurements of DPA subtract from $S_{11}$ measurements of a based-fluid of DMSO.

Further evaluation was conducted on frequencies of interest to verify the relationship of microwave signal responses to varied concentration of DPA. It is interesting to see that varied concentrations of DPA respond to microwaves in a linear trend. FIG. 7 shows the varied concentration of DPA in NaOH responsive well to ($|S_{11}|$) at frequency 2.4 GHz and 4.58 GHZ with a regression of R2=0.9201 and 0.9215 respectively. Whereas FIG. 8 shows the DPA in DMSO at 2.36 GHz and 4.65 GHZ with a regression of R2=0.999 and 0.828.

The sensor according to the invention is a sensing instrument for detecting biological material. While a horn and patch antenna have been used in the examples discussed above, a other antenna structures/types may be used instead to direct microwave radiation to samples (e.g. surfaces) to examine biological material in different samples (e.g. on different surfaces). Different antennas were used for proof of concept i.e. horn antenna and patch antenna. However, it is to be understood that the invention is not limited to these types of antennas.

Figure 9:
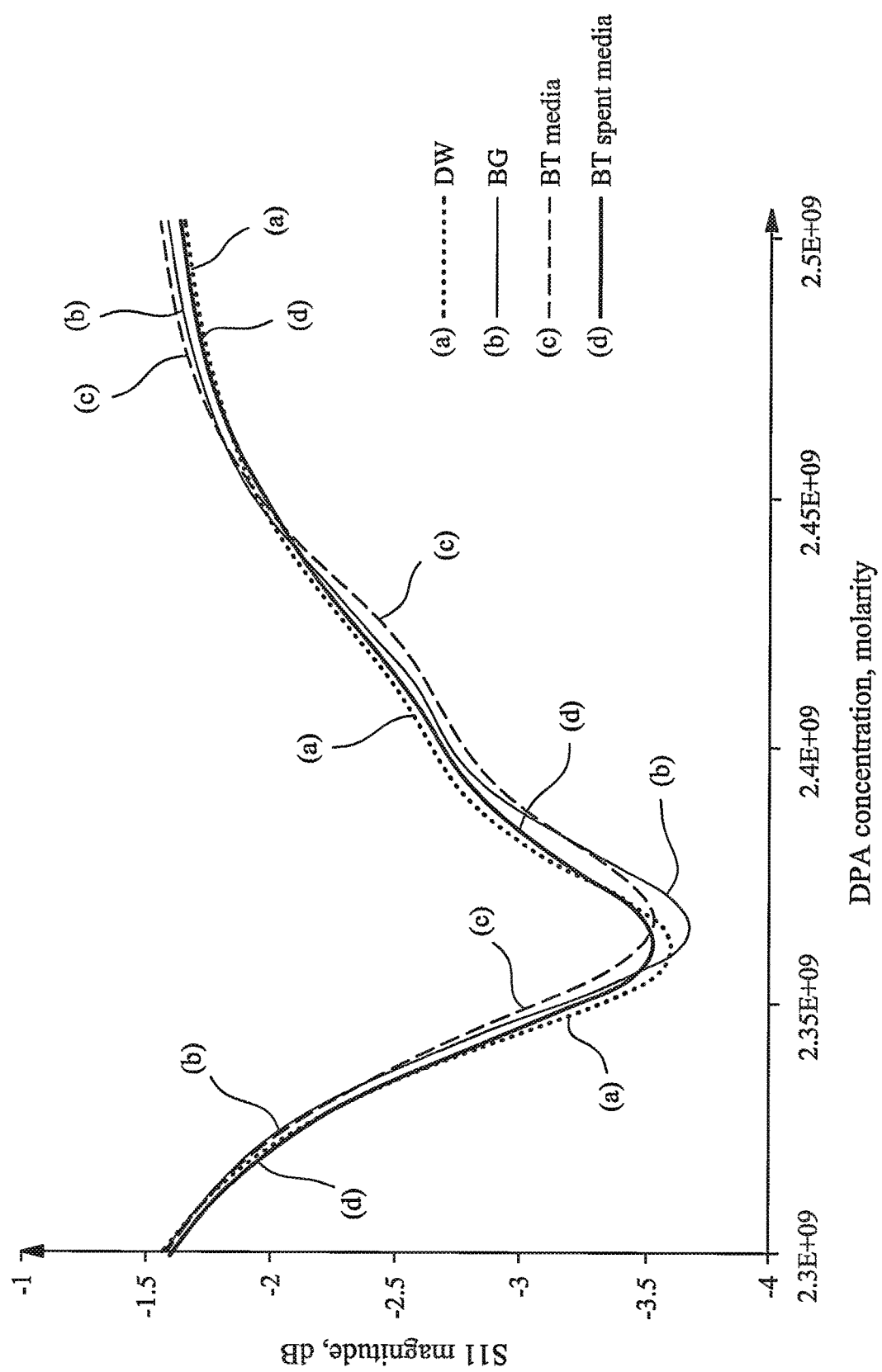
FIG. 9 illustrates multiple spectra of the magnitude of a reflection coefficient ($S_{11}$) of microwave radiation reflected from a sample containing, respectively, three different bacillus species.

Furthermore, different species samples which consists of bacillus globigii (BG), *Bacillus thuringiensis* (BT) media and *Bacillus thuringinensis* (BT) spent media (i.e. depleted of nutrients) at constant concentration of $10^7$. FIG. 9 shows the spectrum of the scalar magnitude of $S_{11}$ (i.e. the value of $|S_{11}|$, as a function of changing microwave probe signal frequency) for 3 different bacillus species over the spectral range from 2.3-2.5 GHz for three different bacillus species. It is seen that different species yielded a different signal spectrum, establishing the detection of bacillus species.

The sensor has been exemplified as used for detection of DPA in solution form, which is the bio-maker of bacillus spores. This example is not intended to be limiting and is for immustrative purposes, to allow a better understanding of the invention. The sensor is able to perform in non-destructive and real time sensing. It is to be undersood that the present disclosure refers to DPA purely as an illustrative example of a biological material detectable within a sample, and that the invention is not limited to DPA detection.

The invention claimed is:

1. A sensor for identifying the presence of a biological material in a sample, the sensor comprising:

an antenna apparatus for transmitting and receiving microwave electromagnetic (EM) signals;

a signal transmitter apparatus coupled to the antenna apparatus and arranged to transmit a microwave-frequency output signal to the antenna apparatus for emission therefrom as an output electromagnetic (EM) signal for reflection at a said sample and to receive a microwave-frequency return signal from the antenna apparatus in response to a return electromagnetic (EM) signal received thereat by reflection from a said sample;

a signal processor arranged to calculate a complex-valued reflection coefficient, comprising a real component and an imaginary component, according to said return signal and said output signal, and to detect the presence of said biological material in said sample according to both the real component and the imaginary component of said reflection coefficient.

2. The sensor for identifying the presence of a biological material according to claim 1 wherein the signal processor apparatus is arranged to subtract a value of a first background component from the value of said real component thereby to generate an adjusted real component of said reflection coefficient, and to subtract a value of a second background component from the value of said imaginary component thereby to generate an adjusted imaginary component of said reflection coefficient, and to detect the presence of said biological material in said sample according to both the adjusted real component and the adjusted imaginary component of said reflection coefficient.

3. The sensor for identifying the presence of a biological material according to claim 2 wherein the first background component and the second background component are the real component and the imaginary component, respectively, of a complex-valued background reflection coefficient stored in the signal processor and corresponding to the absence of said biological material in said sample.

4. The sensor for identifying the presence of a biological material according to claim 3 wherein the adjusted real component and the adjusted imaginary component of said reflection coefficient define a complex vector which is a vector sum of the complex-valued reflection coefficient and the complex-valued background reflection coefficient.

5. The sensor for identifying the presence of a biological material according to claim 1 wherein the microwave-frequency output signal and the microwave-frequency return signal share the same signal frequency.

6. The sensor for identifying the presence of a biological material according to claim 5 in which said signal frequency is in a range from 1.0 GHz to 6.0 GHz.

7. The sensor for identifying the presence of a biological material according to claim 1 wherein the signal transmitter apparatus comprises a signal transceiver unit configured to both transmit said output signal to said antenna apparatus and to receive said return signal from said antenna apparatus.

8. The sensor for identifying the presence of a biological material according to claim 1 wherein the said antenna apparatus comprises a single antenna arranged to emit said output electromagnetic (EM) signal and to receive said return electromagnetic (EM) signal.

9. The sensor for identifying the presence of a biological material according to claim 1 wherein the said antenna apparatus comprises a manually operable hand-held antenna assembly or a directional antenna.

10. The sensor for identifying the presence of a biological material according to claim 1 wherein said biological material comprises dipicolinic acid (DPA).

11. A method for identifying the presence of a biological material in a sample, the method comprising:
by an antenna apparatus, transmitting and receiving microwave electromagnetic (EM) signals;
by a signal transmitter apparatus coupled to the antenna apparatus:
transmitting a microwave-frequency output signal to the antenna apparatus for emission therefrom as an output electromagnetic (EM) signal for reflection at a said sample;
receiving a microwave-frequency return signal from the antenna apparatus in response to a return electromagnetic (EM) signal received thereat by reflection from a said sample;
by a signal processor, calculating a complex-valued reflection coefficient, comprising a real component and an imaginary component, according to said return signal and said output signal, and detecting the presence of said biological material in said sample according to both the real component and the imaginary component of said reflection coefficient.

12. The method for identifying the presence of a biological material in a sample according to claim 11 including, by the signal processor:
subtracting a value of a first background component from the value of said real component thereby to generate an adjusted real component of said reflection coefficient;
subtracting a value of a second background component from the value of said imaginary component thereby to generate an adjusted imaginary component of said reflection coefficient; and
detecting the presence of said biological material in said sample according to both the adjusted real component and the adjusted imaginary component of said reflection coefficient.

13. The method for identifying the presence of a biological material in a sample according to claim 12 wherein the first background component and the second background component are the real component and the imaginary component, respectively, of a complex-valued background reflection coefficient corresponding to the absence of said biological material in a sample.

14. The method for identifying the presence of a biological material in a sample according to claim 13 wherein the adjusted real component and the adjusted imaginary component of said reflection coefficient define a complex vector which is a vector sum of the complex-valued reflection coefficient and the complex-valued background reflection coefficient.

15. The method for identifying the presence of a biological material in a sample according to claim 11 wherein the microwave-frequency output signal and the microwave-frequency return signal share the same signal frequency.

16. The method for identifying the presence of a biological material in a sample according to claim 15 in which said signal frequency is in a range from 1.0 GHz to 6.0 GHz.

17. The method for identifying the presence of a biological material in a sample according to claim 11 including emit said output electromagnetic (EM) signal and receiving said return electromagnetic (EM) signal via a common single antenna.

18. The method for identifying the presence of a biological material in a sample according to claim 11 including emitting said output electromagnetic (EM) signal and receiving said return electromagnetic (EM) signal via a manually operable hand-held antenna assembly.

19. The method for identifying the presence of a biological material in a sample according to claim 11 including emitting said output electromagnetic (EM) signal and receiving said return electromagnetic (EM) signal via directionally via a directional antenna.

20. The method for identifying the presence of a biological material in a sample according to claim 11 wherein said biological material comprises dipicolinic acid (DPA).

* * * * *